United States Patent
Chance et al.

(10) Patent No.: US 6,263,221 B1
(45) Date of Patent: *Jul. 17, 2001

(54) QUANTITATIVE ANALYSES OF BIOLOGICAL TISSUE USING PHASE MODULATION SPECTROSCOPY

(75) Inventors: Britton Chance, Marathon, FL (US); Vasilis Ntziachristos, Philadelphia, PA (US)

(73) Assignee: Non-Invasive Technology, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/799,206

(22) Filed: Feb. 13, 1997

Related U.S. Application Data

(63) Continuation-in-part of application No. 08/731,443, filed on Oct. 15, 1996, which is a continuation of application No. 08/031,945, filed on Mar. 16, 1993, now Pat. No. 5,564,417, which is a continuation-in-part of application No. 08/076,370, filed on Jun. 14, 1993, now Pat. No. 5,553,614, which is a continuation of application No. 07/645,590, filed on Jan. 24, 1991, now abandoned.

(51) Int. Cl.[7] ............................................. A61B 5/00
(52) U.S. Cl. .......................... 600/310; 600/323; 600/336
(58) Field of Search .................................. 600/310, 604, 600/322–343, 407, 473, 476, 472

(56) References Cited

U.S. PATENT DOCUMENTS

| | | | |
|---|---|---|---|
| 5,353,799 | * 10/1994 | Chance | 600/473 |
| 5,402,778 | * 4/1995 | Chance | 600/473 |
| 5,528,365 | * 6/1996 | Gonatas . | |
| 5,596,987 | * 1/1997 | Chance | 600/476 |
| 5,664,574 | * 9/1997 | Chance | 600/476 |
| 5,673,701 | * 10/1997 | Chance | 600/476 |
| 5,779,631 | * 7/1998 | Chance | 600/473 |
| 5,782,755 | * 7/1998 | Chance et al. | 600/476 |
| 5,792,051 | * 8/1998 | Chance | 600/473 |
| 5,807,263 | * 9/1998 | Chance | 600/476 |
| 5,820,558 | * 10/1998 | Chance | 600/473 |
| 5,853,370 | * 12/1998 | Chance et al. | 600/473 |

* cited by examiner

*Primary Examiner*—David M. Shay
(74) *Attorney, Agent, or Firm*—Fish & Richardson, P.C.

(57) ABSTRACT

A spectroscopic system for quantifying in vivo concentration of an absorptive pigment in biological tissue includes an oscillator for generating a first carrier waveform of a first frequency on the order of $10^8$ Hz, a light source for generating light of a selected wavelengths modulated by the carrier waveform, and a detector for detecting radiation that has migrated over photon migration paths in the tissue from an input port to a detection port spaced several centimeters apart. The wavelength is sensitive to concentration of an absorptive pigment present in the tissue. A phase detector compares the detected radiation with the introduced radiation and determines therefrom the phase shift of the detected radiation. A processor quantifies the concentration of the absorptive pigment by calculating a value of the absorption coefficient.

36 Claims, 11 Drawing Sheets

QUANTITATIVE ANALYSES OF BIOLOGICAL TISSUE USING PHASE MODULATION SPECTROSCOPY

CROSS REFERENCE TO RELATED APPLICATION

This application is a continuation-in-part of U.S. patent application Ser. No. 08/731,443, filed Oct. 15, 1996; which in turn is a continuation of U.S. patent application Ser. No. 08/031,945, filed Mar. 16, 1993, now U.S. Pat. No. 5,564, 417; which in turn is a continuation-in-part of U.S. patent application Ser. No. 08/076,370, filed Jun. 14, 1993, issued as U.S. Pat. No. 5,553,614; which is a continuation of U.S. patent application Ser. No. 07/645,590, filed Jan. 24, 1991, now abandoned, all of which are incorporated by reference as if fully set forth herein.

BACKGROUND OF THE INVENTION

The present invention relates to quantitative analyses of absorptive constituents in biological tissues by employing a phase modulation spectroscopy.

Continuous wave (CW) tissue oximeters have been widely used to determine in vivo concentration of an optically absorbing pigment (e.g., hemoglobin, oxyhemoglobin) in biological tissue. The CW oximeters measure attenuation of continuous light in the tissue and evaluate the concentration based on the Beer Lambert equation or a modified Beer Lambert absorbance equation. The Beer Lambert equation (1) describes the relationship between the concentration of an absorbent constituent (C), the extinction coefficient ($\epsilon$), the photon migration pathlength $<L>$, and the attenuated light intensity ($I/I_o$).

$$\frac{\log[I/I_0]}{\langle L \rangle} = \sum \epsilon_i C_i \quad (1)$$

The CW spectrophotometric techniques can not determine $\epsilon$, C, and $<L>$ at the same time. If one could assume that the photon pathlength were constant and uniform throughout all subjects, direct quantitation of the constituent concentration (C) using CW oximeters would be possible.

In tissue, the optical migration pathlength varies with the size, structure, and physiology of the internal tissue examined by the CW oximeters. For example, in the brain, the gray and white matter and the structures thereof are different in various individuals. In addition, the photon migration pathlength itself is a function of the relative concentration of absorbing constituents. As a result, the pathlength through an organ with a high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. Thus, where possible, it is advantageous to measure the pathlength directly when quantifying the hemoglobin concentration in tissue.

SUMMARY OF THE INVENTION

In general, in one aspect, a spectroscopic system for quantifying in vivo concentration of an absorptive pigment in biological tissue includes an oscillator constructed to generate a first carrier waveform of a first frequency on the order of $10^8$ Hz (i.e., in the range of 10 MHz to 1 GHz), a light source, operatively coupled to the oscillator, constructed to generate electromagnetic radiation of a selected wavelengths modulated by the carrier waveform, and a detector constructed to detect radiation that has migrated over photon migration paths in the tissue from an input port to a detection port spaced several centimeters apart. The wavelength is sensitive to concentration of the absorptive pigment present in the tissue. A phase detector is constructed to compare the detected radiation with the introduced radiation and determine therefrom the phase shift of the detected radiation at each wavelength. A processor is constructed to receive the phase shift and a scattering property of the portion of the tissue and calculate a value of the absorption coefficient, at the wavelength, using Eq. 4.

In another embodiment, the spectroscopic system includes a light source further constructed to generate electromagnetic radiation of a second wavelengths modulated by the carrier waveform. At least one of the wavelengths is sensitive to concentration of an absorptive pigment present in the tissue, while the tissue exhibits similar scattering properties at the two wavelengths. The detector is constructed to detect the radiation at the second wavelength. The phase detector is constructed to compare the detected radiation with the introduced radiation and determine therefrom the phase shift at the second wavelength. The processor is constructed to receive the phase shift at the second wavelength and calculate a value of the absorption coefficient, at the second wavelength, using Eq. 4.

In general, in one aspect, a spectroscopic system for quantifying in vivo concentration of an absorptive pigment in biological tissue includes an oscillator constructed to generate a first carrier waveform of a first frequency on the order of $10^8$ Hz (i.e., in the range of 10 MHz to 1 GHz), a light source, operatively coupled to the oscillator, constructed to generate electromagnetic radiation of a selected wavelengths modulated by the carrier waveform, and a detector constructed to detect radiation that has migrated over photon migration paths in the tissue from an input port to a detection port spaced several centimeters apart. The wavelength is sensitive to concentration of the absorptive pigment present in the tissue. The spectroscopic system also includes a phase splitter, two double balanced mixers, and a processor. The phase splitter is constructed to receive the carrier waveform and produce first and second reference phase signals of predefined substantially different phases. The first and second double balanced mixers are connected to receive from the phase splitter the first and second reference phase signals, respectively, and are connected to receive from the detector the detector signal, in order to produce therefrom a real output signal and an imaginary output signal, respectively. The processor is constructed to receive a scattering property of the portion of the tissue and is constructed to quantify the concentration of the absorptive pigment by calculating phase shift ($\theta$) of the detected radiation as the inverse tangent of the ratio of the imaginary output signal and the real output signal. The processor also calculates a value of the absorption coefficient, at the wavelength, using Eq. 4.

In another embodiment, the spectroscopic system includes a light source further constructed to generate electromagnetic radiation of a second wavelengths modulated by the carrier waveform. At least one of the wavelengths is sensitive to concentration of an absorptive pigment present in the tissue, while the tissue exhibits similar scattering properties at the two wavelengths. The detector is constructed to detect the radiation at the second wavelength. The first and second double balanced mixers are connected to receive from the phase splitter the first and second reference phase signals, respectively, and connected to receive from the detector the detector signal at the second wavelength. The mixers are constructed to produce therefrom a real output signal and an imaginary output signal, respectively, at the second wavelength. The processor is constructed to quantify the concentration of the absorptive pigment by calculating phase shift ($\theta$) of the detected radiation as the inverse tangent of the ratio of the imaginary output signal and the real output signal and by calculating a value of the absorption coefficient, at the wavelength, using Eq. 4.

As different embodiments, the spectrophotometer may be a dual wavelength, single frequency system or a dual wavelength, dual frequency system. Each system can measure data for a single source-detector separation (i.e., separation of the input port and the detection port) or for several source-detector separations.

Different embodiments of the spectrophotometer may include one or more of the following features.

The spectrophotometer may include a second oscillator constructed to generate a second carrier waveform of a second selected frequency on the order of $10^8$ Hz, while the tissue exhibits similar scattering properties at the selected frequencies. The source is operatively coupled to the second oscillator and is constructed to generate electromagnetic radiation of the two wavelengths modulated by the second carrier waveform. The detector is further constructed to detect the radiation modulated by the second carrier waveform. The phase detector is further constructed to compare, at each wavelength, the detected radiation of the second carrier waveform with the introduced radiation and determine therefrom the phase shift of the detected radiation.

The processor may calculate a ratio of absorption coefficients at the two wavelengths, and calculate a value of oxygen saturation based on the ratio.

The spectrophotometer may include a look up table including values of the scattering property for different tissue types. These values may be the effective scattering coefficient, $(1-g)\mu_s$.

The absorptive pigment may be oxyhemoglobin or deoxyhemoglobin.

DESCRIPTION OF THE PREFERRED EMBODIMENTS

One preferred embodiment of the pathlength corrected oximeter utilizes three LEDs for generation of light at three selected wavelengths intensity modulated at a frequency of 50.1 MHz and coupled directly to the examined tissue. At each wavelength, the introduced light is altered by the tissue and is detected by a wide area photodiode placed against the skin. The introduced and detected radiations are compared to determine their relative phase shift that corresponds to an average pathlength of the migrating photons and, furthermore, the light attenuation is determined.

Figure 1:
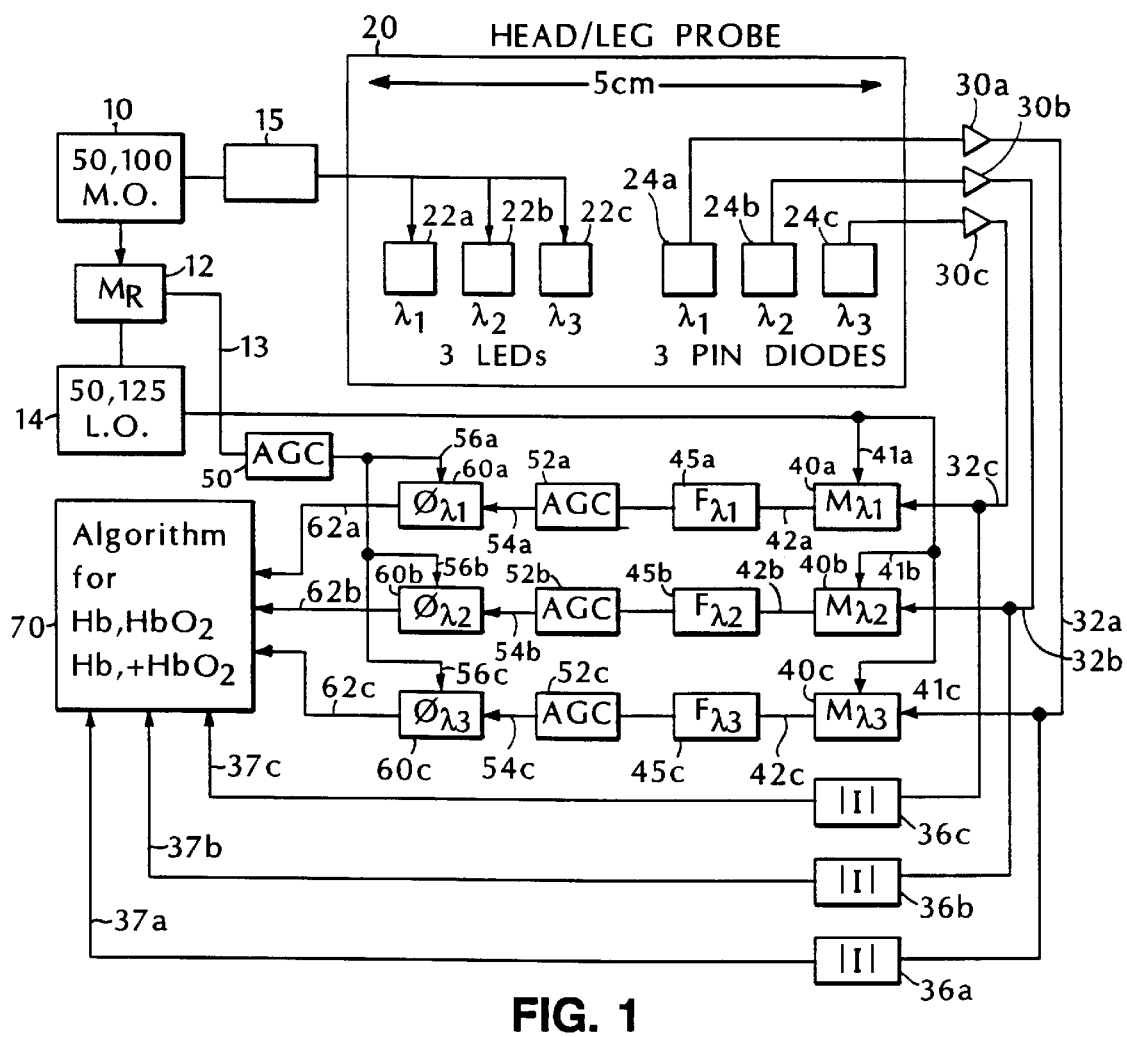
FIG. 1 is a block diagram of a pathlength corrected oximeter in accordance with the present invention.

Referring to FIG. 1, the oximeter includes a master oscillator 10 operating at 50.1 MHz connected to a power amplifier 15 of sufficient output power to drive LEDs 22a, 22b, and 22c (for example HLP 20RG or HLP 40RG made by Hitachi) that emit 760 nm, 840 nm, and 905 nm (or 950 nm) light, respectively. A second local oscillator 14 operating at 50.125 MHz and mixer 12 are used to generate a reference frequency 13 of 25 kHz. Each LED directly positioned on the skin has an appropriate heat sink to eliminate uncomfortable temperature increases that could also alter blood perfusion of the surrounding tissue. Three PIN diode detectors 24a, 24b, and 24c are placed at a distance of approximately 5 cm from the LEDs and have a detection area of about 1 cm². Photons migrating a few centimeters deep into the tissue are detected by the respective PIN diodes. The source-detector separation can be increased or decreased to capture deeper or shallower migrating photons. The signals from PIN diodes 24a, 24b, and 24c are amplified by preamplifiers 30a, 30b, and 30c, respectively.

The amplified signals (32a, 32b, 32c) are sent to magnitude detectors 36a, 36b, and 36c and to mixers 40a, 40b, and 40c, respectively. The magnitude detectors are used to determine intensity values of detected signals at each wavelength to be used in Eq. 1. Each mixer, connected to receive a 50.125 MHz reference signal (41a, 41b, 41c) from local oscillator 14, converts the detection signal to a 25 kHz frequency signal (42a, 42b, 42c). The mixers are high dynamic range frequency mixers, model SRA-1H, commercially available from Mini-Circuits (Brooklyn N.Y.). The detection signals (42a, 42b, and 42c) are filtered by filters 45a, 45b, 45c, respectively.

Phase detectors 60a, 60b, and 60c are used to determine phase shift between the input signal and the detected signal at each wavelength. Each phase detector receives the 25 kHz detection signal (54a, 54b, 54c) and the 25 kHz reference signal (56a, 56b, 56c), both of which are automatically leveled by automatic gain controls 50 and 52 to cover the dynamic range of signal changes. Phase detectors 60a, 60b, and 60c generate phase shift signals (62a, 62b, 62c) corresponding to the migration delay of photons at each wavelength. Each phase shift signal is proportional to the migration pathlength used in calculation algorithms performed by processor 70.

Figure 2:
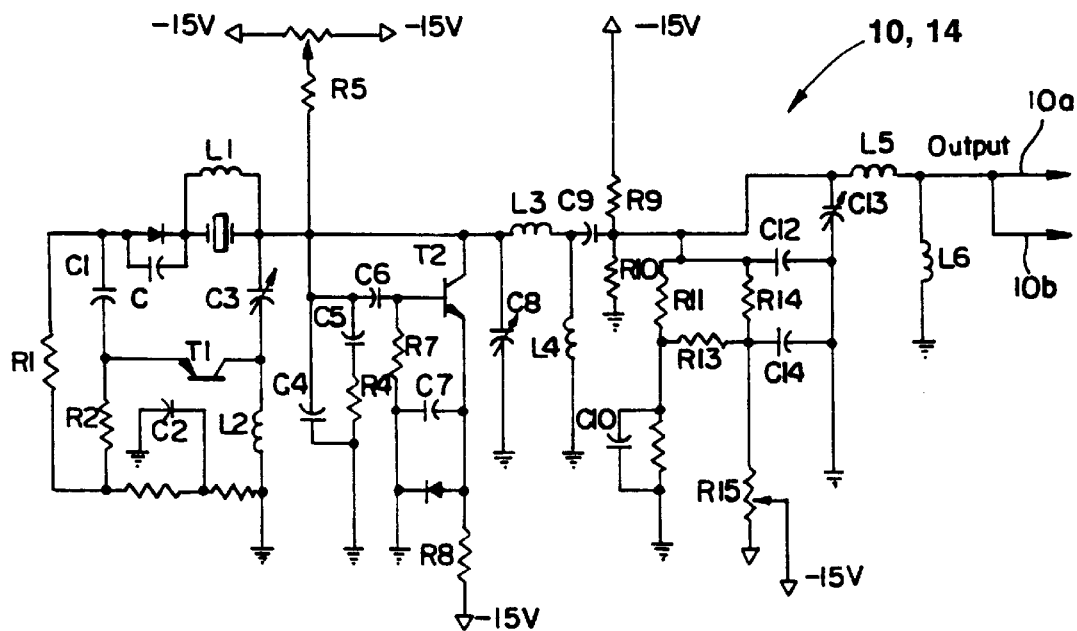
FIG. 2 is a schematic circuit diagram of a 50.1 MHz (50.125 MHz) oscillator used in the oximeter of FIG. 1.

FIG. 2 shows a schematic circuit diagram of a precision oscillator used as the 50.1 MHz master oscillator 10 and 50.125 MHz local oscillator 14. The oscillator crystals are neutralized for operation in the fundamental resonance mode; this achieves long-term stability. Both oscillators are thermally coupled so that their frequency difference is maintained constant at 25 kHz if a frequency drift occurs.

Figure 3:
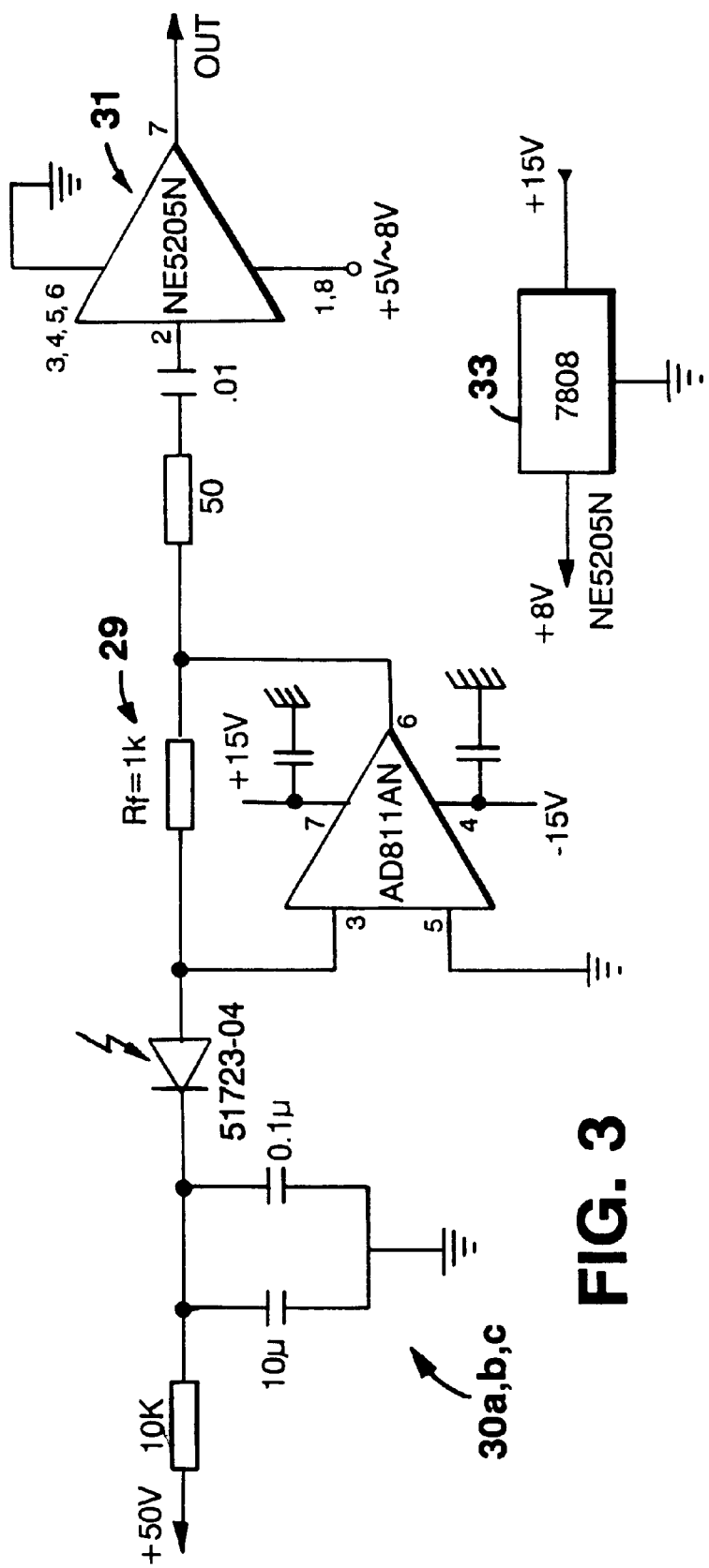
FIG. 3 is a schematic circuit diagram of a PIN diode and a preamplifier used in the oximeter of FIG. 1.
Figure 4:
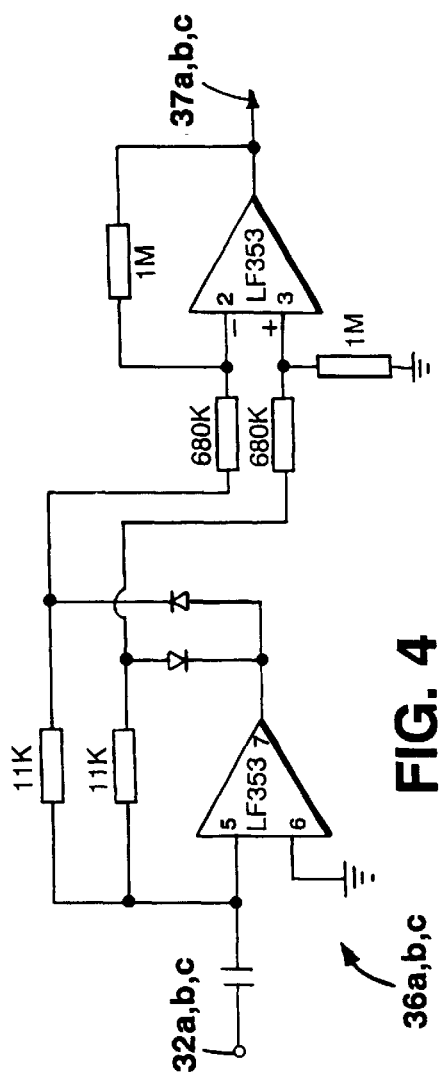
FIG. 4 is a schematic circuit diagram of a magnitude detector used in the oximeter of FIG. 1.

PIN diodes 24a, 24b, and 24c are directly connected to their respective preamplifiers 30a, 30b, and 30c, as shown in FIG. 3. The oximeter uses PIN silicon photodiodes S1723-04 with 10 mm×10 mm sensitive area and spectral response in the range of 320 nm to 1060 nm. The detection signal is amplified by stages 29 and 31, each providing about 20 dB amplification. The NE5205N operational amplifier is powered at +8V to operate in a high gain regime. The 8V signal is supplied by a voltage regulator 33. The amplified detection signals (32a, 32b, and 32c) are sent to magnitude detectors 36a, 36b, and 36c, shown in FIG. 4. The magnitude values (37a, 37b, and 37c) are sent to processor 70 that calculates the light attenuation ratio or logarithm thereof as shown Eq. 1.

Figure 5:
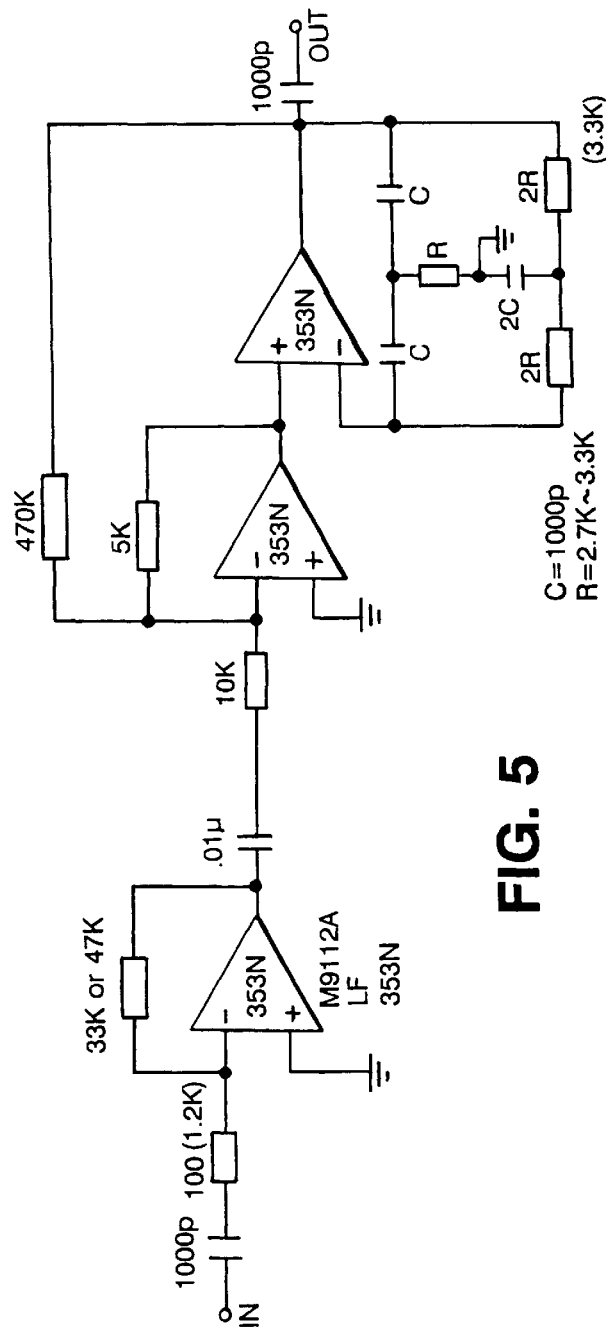
FIG. 5 is a schematic circuit diagram of a 25 kHz filter used in the oximeter of FIG. 1.

Also referring to FIG. 5, the AGC circuit uses MC 1350 integrated circuit for amplification that maintains the input signal of phase detector 60 at substantially constant levels. The amount of gain is selected to be equal for AGCs, 50 and 52. The signal amplitude is controlled by a feedback network 53. The AGCs provide a substantially constant amplitude of the detected and reference signals to eliminate variations in the detected phase shift due to cross talk between amplitude and phase changes in the phase detector.

Figure 6:
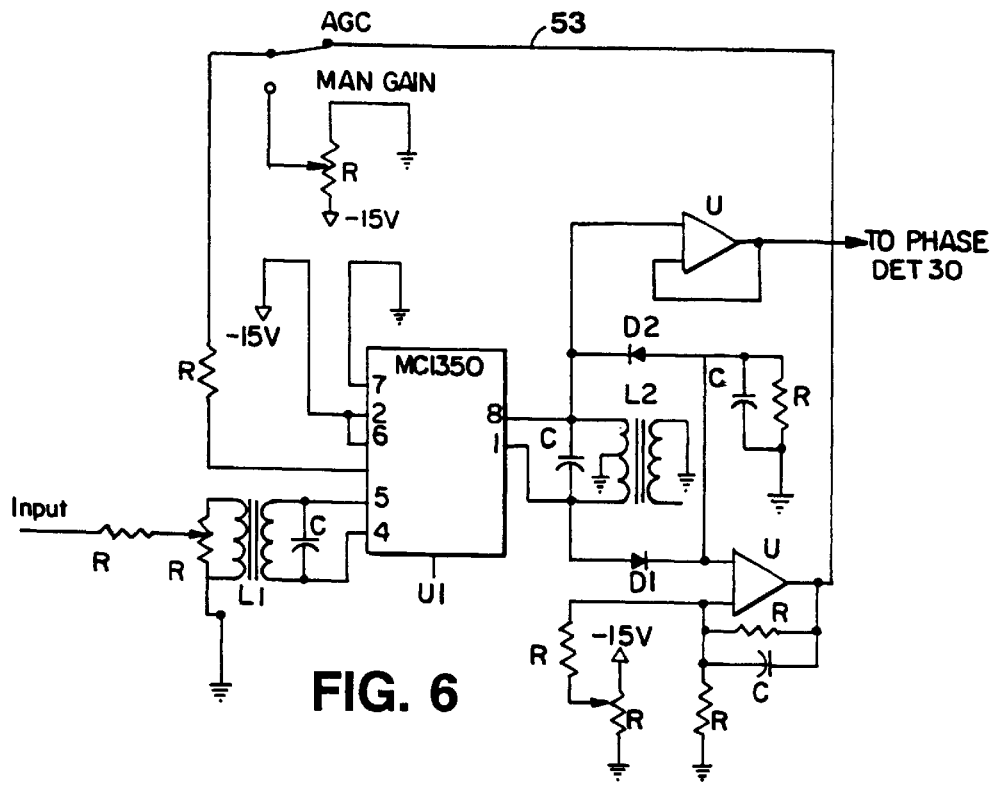
FIG. 6 is a schematic diagram of an AGC circuit of the oximeter of FIG. 1.
Figure 7:
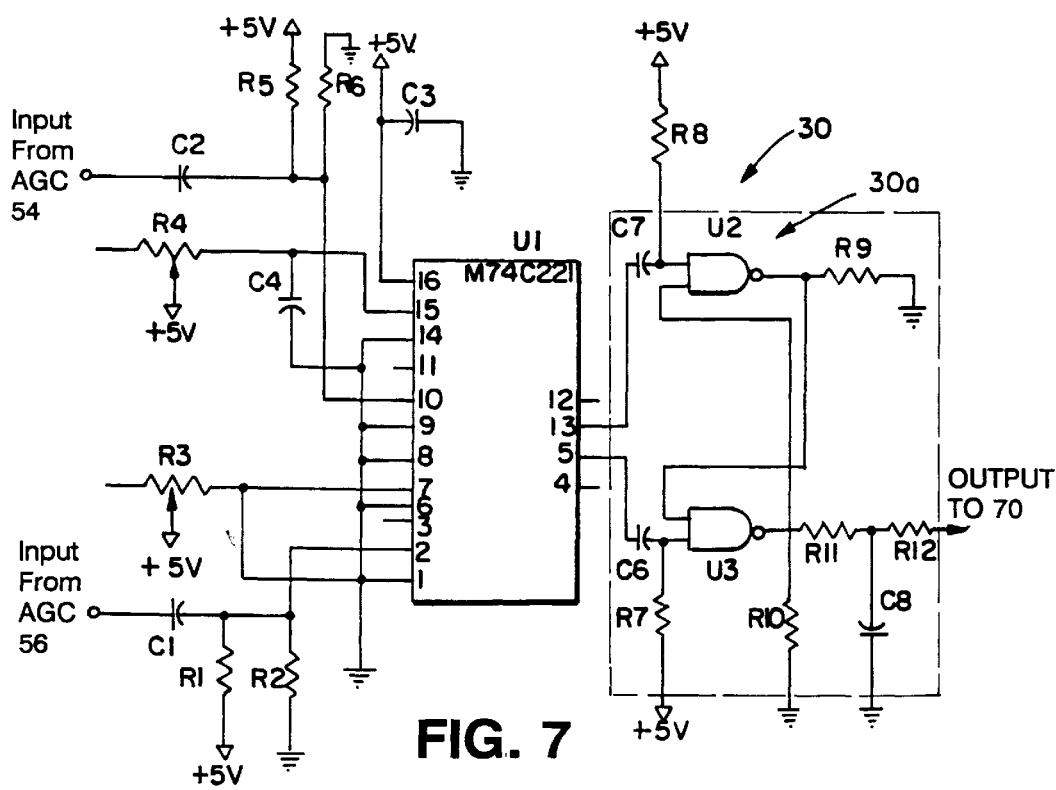
FIG. 7 is a schematic circuit diagram of a phase detector of the oximeter of FIG. 1.

Referring to FIG. 6, each phase detector includes a Schmitt trigger that converts the substantially sinusoidal detection signal (54a, 54b, 54c) and reference signal (56a, 56b, 56c) to square waves. The square waves are input to a detector that has complementary MOS silicon-gate transistors. The phase shift signal is sent to processor 70.

The oximeter is calibrated by measuring the phase shift for a selected distance in a known medium, i.e., using a standard delay unit, and by switching the length of a connector wire to change the electrical delay between master oscillator 10 and local oscillator 14.

Figure 8A:
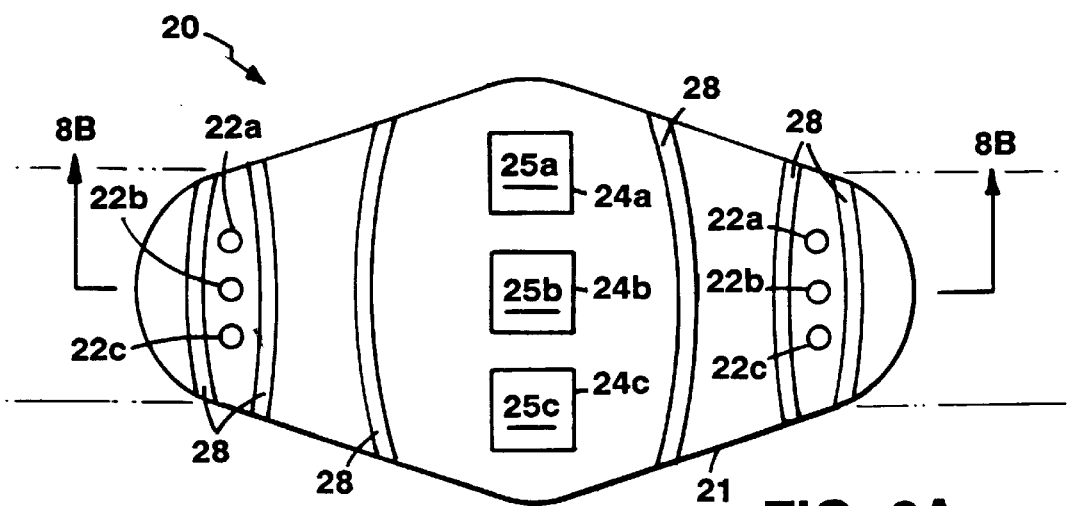
FIG. 8A is a plan view of a source-detector probe of the oximeter.
Figure 8B:
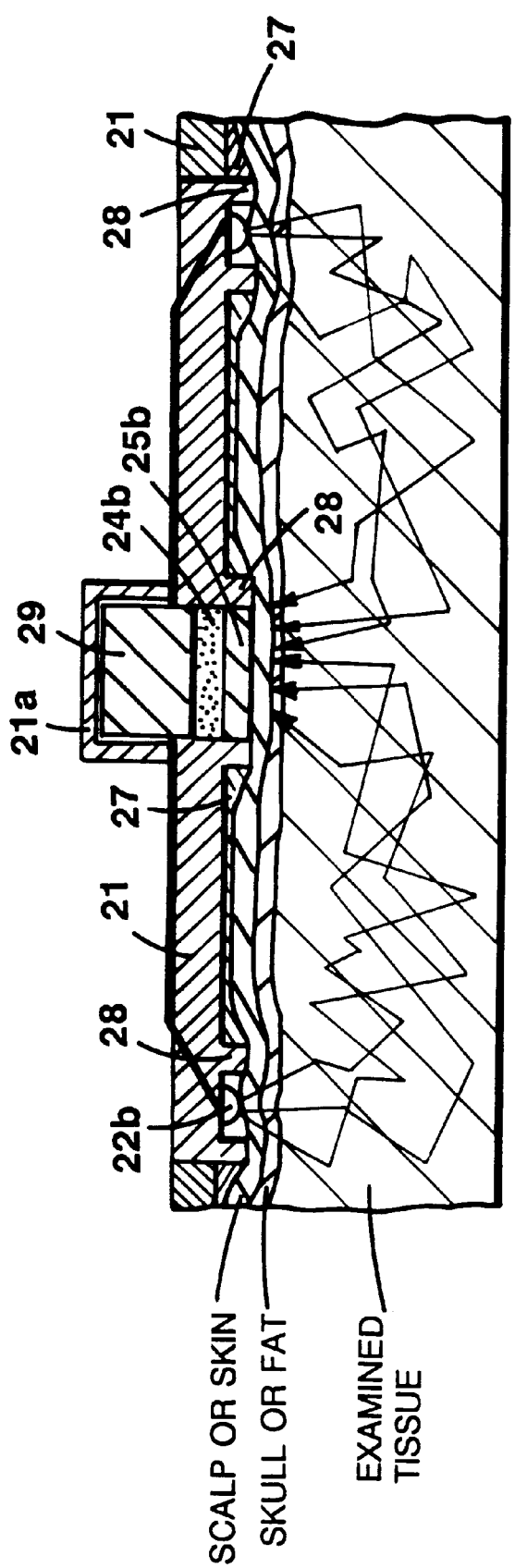
FIG. 8B is a transverse cross-sectional view taken on lines 8B of FIG. 8A further showing the photon migration.

Referring to FIGS. 8A and 8B source-detector probe 20 includes several LEDs (22a, 22b, 22c) of selected wavelengths and PIN photodiodes (24a, 24b, 24c) mounted in a body-conformable support structure 21. Structure 21 also includes a photon escape barrier 27 made of a material with selected scattering and absorption properties (for example, styrofoam) designed to return escaping photons back to the examined tissue. The support structure further includes a second conformable barrier 28, located between the LEDs and the diode detectors, designed to absorb photons directly propagating from the source to the detector and thus prevent detection of photons that migrate subcutaneously. Support structure 21 also includes electronic circuitry 29 encapsulated by an electronic shield 21a.

Each PIN diode is provided with an evaporated single wavelength film filter (25a, 25b, 25c). The filters eliminate the cross talk of different wavelength signals and allow continuous operation of the three light sources, i.e., no time sharing is needed.

The use of photodiode detectors has substantial advantages when compared with the photomultiplier tube used in standard phase modulation systems. The photodiodes are placed directly on the skin, i.e., no optical fibers are needed. Furthermore, there is no need to use a high voltage power supply that is necessary for the photomultiplier tube. The photodiodes are much smaller and are easy to place close to the skin. Advantages of the photomultiplier tube are a huge multiplication gain and a possibility of direct mixing at the photomultiplier; this cannot be achieved directly by a photodiode. This invention envisions the use of several different photodiodes such as PIN diode, avalanche diode, and other.

The processor uses algorithms that are based on equations described by E. M. Sevick et al. in "Quantitation of Time- and Frequency-Resolved Optical Spectra for the Determination of Tissue Oxygenation," published in Analytical Biochemistry 195, 330, Apr. 15, 1991, which is incorporated by reference as if fully set forth herein. The photon migration in biological tissue is a diffusional process in which the photon fluence rate, $\phi(r,t)$, is distributed from the source. The fluence rate is equal to $N_\alpha$ c, or the product of the number of the photon at position r and time, t, and the speed of photons through the medium. The fluence rate, or the effective "concentration" of photons at position r and time t, in the tissue or turbid media may be obtained from the solution of the general diffusion equation $$\frac{1}{c}\frac{\partial}{\partial t}\phi(r,\,t) - D\nabla^2 \phi(r,\,t) + \mu_a \phi(r,\,t) = S(r,\,t) \quad (2)$$

where D is the diffusion coefficient and S a source term. For photon migration, the diffusion coefficient is equal to $$D = \frac{1}{3\mu_a + (1-g)\mu_s} \quad (3)$$

where $\mu_s$ is the scattering coefficient (cm$^{-1}$) and g is the mean cosine of scattering angle. The term $(1-g)\mu_s$ is referred to as the effective scattering coefficient and is equal to the reciprocal of the isotropic, mean scattering length, l* (i.e., when the direction of scatter is completely random). The absorption coefficient $\mu_a$ is based upon the Napierian extinction coefficient.

The source at $\rho=0$ consists of light whose intensity is sinusoidally modulated at a frequency f. The light intensity detected at a distance $\rho$ away from the source is both amplitude demodulated and phase shifted with respect to the incident source intensity. The measured phase shift, $\theta$, and the modulation, M, of the detected light with respect to that of the incident light characterize the tissue wherein the detected photons migrated over a distribution of pathlengths. The phase shift describes the pathlength distribution in the frequency domain. It can be directly related to the mean of the distribution of pathlengths traveled by photons before detection. The modulation of the detected intensity also varies with changes in the absorbance and pathlength distribution. Pathlengths can be used to detect changes in absorption in strongly scattering media. Modulation may also be used to detect changes in absorption in the tissue. In phase modulation (frequency modulation), the source term represents a sinusoidally modulated photon flux at point $\rho=0; S(\rho=0,t)=A+M\cdot\sin(2\pi f\cdot t)$. Expressions of the phase shift and modulation of the detected intensity may also be directly found from Eq. 2.

The analytical solution for $\theta$ and M can be obtained from the sine and cosine Fourier transforms of Eq. 2:

$$\theta(\rho, f) = -\psi\sin\frac{\Theta}{2} - \tan^{-1}\frac{-\psi\sin\frac{\Theta}{2}}{1+\psi\cos\frac{\Theta}{2}} \quad (4)$$

-continued $$M(\rho, f) = \frac{\left(1 + \psi^2 + 2\psi\cos\frac{\Theta}{2}\right)^{1/2}}{(1 + \psi_\infty)} \exp\left(\psi_\infty - \psi\cos\frac{\Theta}{2}\right) \quad (5)$$

where:

$$\psi = \sqrt{3(1-g)\mu_s\rho^2\{(\mu_a c)^2 + (2\pi f)^2\}^{1/2} c^{-1}}, \; \psi_\infty = \psi(f = 0) \quad (6)$$

$$\Theta = \tan^{-1}\left\{\frac{2\pi f}{\mu_a c}\right\} \quad (7)$$

At each wavelength, for low modulation frequencies, i.e., $2\pi f \ll \mu_a \cdot c$, the phase shift ($\theta^\lambda$) (62a, 62b, 62c) is used to calculate the pathlength as follows:

$$\theta^\lambda = \tan^{-1}\pi f\langle t^\lambda\rangle = \tan^{-1}\frac{2\pi f\langle L^\lambda\rangle}{c} \approx \frac{2\pi f\langle L^\lambda\rangle}{c} \quad (8)$$

wherein f is modulation frequency of the introduced light which is in the range of 10 MHz to 100 MHz; $t^\lambda$ is the photon migration delay time; c is the speed of photons in the scattering medium; and $L^\lambda$ is the migration pathlength. The modulation frequency of 50 MHz was selected due to the frequency limitation of the LEDs and photodiodes. However, for faster LEDs and photodiodes it may be desirable to use higher modulation frequencies that increase the phase shift resolution.

At high modulation frequencies, i.e., $2\pi f \gg \mu_a \cdot c$, the phase shift is no longer proportional to the mean time of flight <t>.

$$\theta^\lambda = a\rho\sqrt{(1-g)\mu_s}f\left\{1 - \frac{\mu_a^\lambda c}{4\pi f}\right\} \quad (9)$$

$$\theta_0^\lambda = a\rho\sqrt{(1-g)\mu_s}f\left\{1 - \frac{\alpha^\lambda c}{4\pi f}\right\} \quad (10)$$

wherein $\rho$ is the source-detector separation; $a=(6\pi/c)^{1/2}\sin\pi/4$; $(1-g)\mu_s$ is the effective scattering coefficient, $\mu_a^\lambda$ is the absorption coefficient at wavelength $\lambda$, $\alpha^\lambda$ is the background absorbance at wavelength $\lambda$, and $\theta_0^\lambda$ thus represents background scattering and absorption. At two wavelengths, the ratio of absorption coefficients is determined as follows:

$$\frac{\mu_a^{\lambda_1}}{\mu_a^{\lambda_2}} = \frac{\theta^{\lambda_1} - \theta_0^{\lambda_1}}{\theta^{\lambda_2} - \theta_0^{\lambda_2}} \quad (11)$$

The wavelengths are in the visible and infra-red range and are selected to have absorbance sensitive (or insensitive) to various tissue components such as water, cytochrome iron and copper, oxy- and deoxygenated forms of hemoglobin, myoglobin, melanin, glucose and other.

For oxygenated and deoxygenated hemoglobin, the absorption coefficient written in terms of Beer Lambert relationship is as follows:

$$\mu_a^{\lambda_1} = \epsilon_{Hb}^{\lambda_1}[Hb] + \epsilon_{HbO}^{\lambda_1}[HbO_2] + \alpha^{\lambda_1} \quad (12)$$

wherein $\epsilon_{Hb}^{\lambda_1}$ and $\epsilon_{HbO}^{\lambda_1}$ are extinction coefficients for hemoglobin and deoxyhemoglobin that can be stored in a look up table; [Hb], [HbO$_2$] are the tissue concentration of hemoglobin and oxyhemoglobin, respectively; $\alpha^{\lambda_1}$ is background absorbance at wavelength $\lambda_1$.

Tissue hemoglobin saturation can also be determined from dual-wavelength, dual-frequency measurements of the phase shift. For high modulation frequencies, $(2\pi f_1 \gg \mu_a^{\lambda_1}c$ and $f_2 \gg \mu_a^{\lambda_2}c)$ the differences in the measured phase shift at one wavelength and two frequencies can be expressed as $$\frac{\theta_{f_1}^{\lambda_1}}{\sqrt{f_1}} - \frac{\theta_{f_2}^{\lambda_1}}{\sqrt{f_2}} = \sqrt{\frac{6\pi(1-g)\mu_s\rho^2}{c}} \sin\frac{\pi}{4} \frac{\mu_a^{\lambda_1}}{4\pi}\left\{\frac{1}{f_2} - \frac{1}{f_1}\right\} \quad (13)$$

The ratio of this difference measured at two wavelengths can thus be written $$\frac{(\theta_{f_1}^{\lambda_1}/\sqrt{f_1}) - (\theta_{f_2}^{\lambda_1}/\sqrt{f_2})}{(\theta_{f_1}^{\lambda_2}/\sqrt{f_1}) - (\theta_{f_2}^{\lambda_2}/\sqrt{f_2})} = \frac{\mu_a^{\lambda_1}}{\mu_a^{\lambda_2}}. \quad (14)$$

Since the scattering coefficient is wavelength-insensitive over the near-infrared range employed, this dual-frequency, dual-wavelength phase modulated spectroscopy can be used to obtain the ratio of absorption coefficients.

Furthermore, as predicted from the diffusion approximation, the magnitude of the phase shift increases with the source-detector separation, $\rho$. Thus, in homogeneous tissues, the phase shifts measured for several $\rho$ can be used to calculate the absorption and scattering coefficients. These coefficients can be used either by employing Eq. 4 or the equations for the high and low approximations. Similarly, the magnitude of the detected radiation can be measured for different source-detector separations, and the absorption and scattering coefficients can be calculated by using Eq. 5.

The hemoglobin saturation is conventionally defined as follows:

$$Y = \frac{[HbO_2]}{[Hb] + [HbO_2]} \quad (15)$$

For a three wavelength measurement, the hemoglobin saturation can be calculated using Eqs. (12) and (15) as follows:

$$Y = \frac{a(\epsilon_{Hb}^{\lambda_3} - \epsilon_{Hb}^{\lambda_2}) - (\epsilon_{Hb}^{\lambda_1} - \epsilon_{Hb}^{\lambda_2})}{[(\epsilon_{HbO_2}^{\lambda_1} - \epsilon_{HbO_2}^{\lambda_2}) - (\epsilon_{Hb}^{\lambda_1} - \epsilon_{Hb}^{\lambda_2})] - a[(\epsilon_{HbO_2}^{\lambda_3} - \epsilon_{HbO_2}^{\lambda_2}) - (\epsilon_{Hb}^{\lambda_3} - \epsilon_{Hb}^{\lambda_2})]} \quad (16)$$

where $$a = \frac{\mu_a^{\lambda_1} - \mu_a^{\lambda_2}}{\mu_a^{\lambda_3} - \mu_a^{\lambda_2}} \quad (17)$$

Thus, processor 70 determines Y from the above equations for each wavelength $\lambda_1$, $\lambda_2$, $\lambda_3$.

In another embodiment, the spectrophotometer's electronics includes a low frequency module suitably and a high frequency module switchably coupled to the same source-detector probe 20. The low frequency module and the arrangement of the source-detector probe are substantially similar to the hemoglobinometer described in a co-pending U.S. patent application Ser. No. 701,127 filed May 16, 1991 which is incorporated by reference as if fully set forth herein. The low frequency module corresponds to a standard oximeter with modulation frequencies in the range of a few hertz to $10^4$ hertz and is adapted to provide intensity attenuation data at two or three wavelengths. Then, the LEDs are switched to the high frequency phase modulation unit, similar to the unit of FIG. 1, which determines the average pathlength at each wavelength. The attenuation and pathlength data are sent to processor 70 for determination of a physiological property of the examined tissue.

Figure 9:
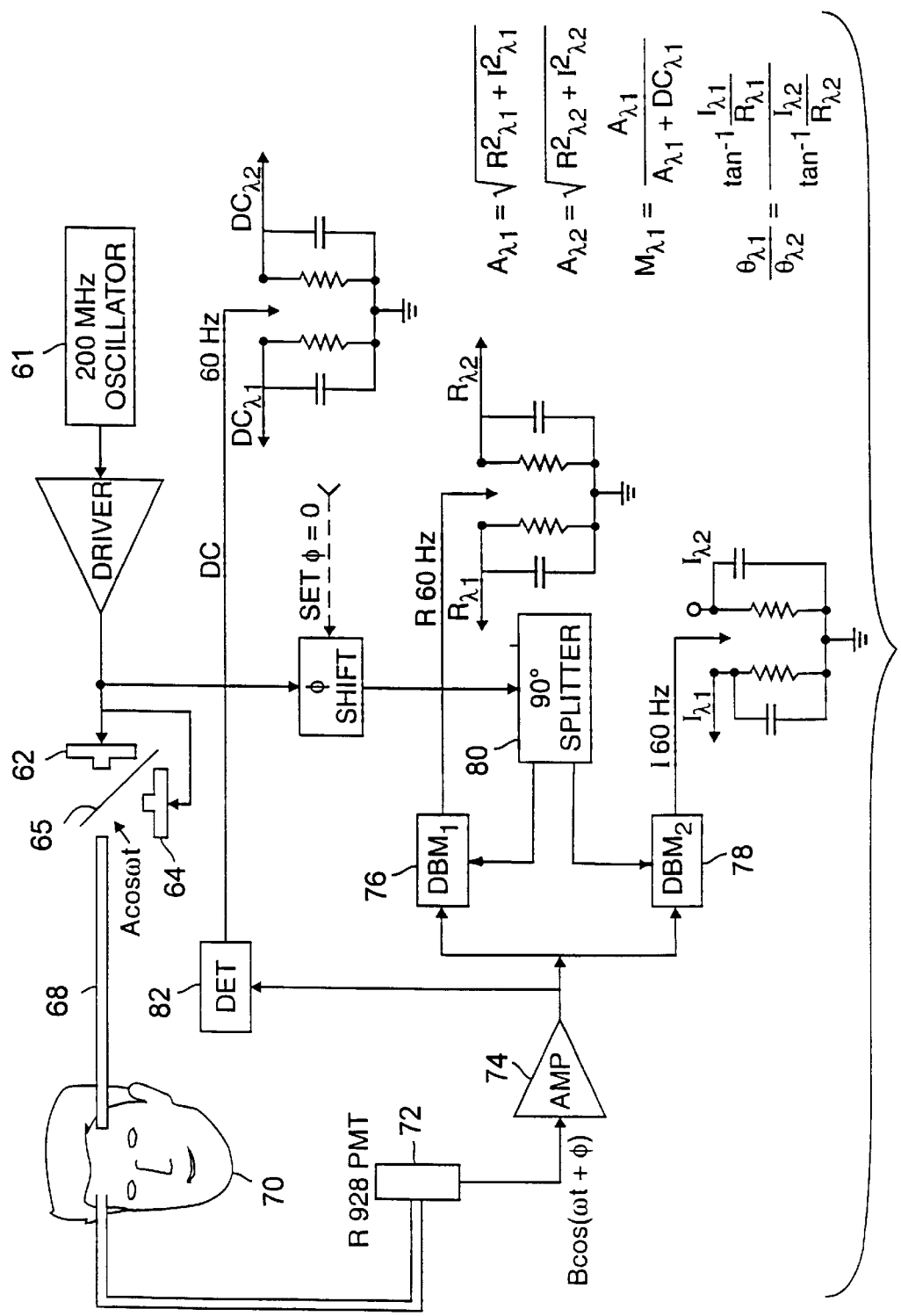
FIG. 9 is a block diagram of another embodiment of a phase modulation spectrophotometer.

In another embodiment, the pathlength corrected oximeter utilizes the same LED sources (22a, 22b, 22c) sinusoidally modulated at a selected frequency comparable to the average migration time of photons scattered in the examined tissue on paths from the optical input port of the LED's to the optical detection part of the photodiode detectors (24a, 24b, 24c), but the electronic circuitry is different. Referring to FIG. 9, this embodiment utilizes a 200 MHz precision oscillator 61, which drives two laser diodes 62 and 64, again at 760 and 816 nm. The outputs of the laser diodes are time shared into filter optic coupling 68 and the head 70. Detector 72 provides output to an amplifier 74 and to two wide band double balance mixers (DBM) 76 and 78 which are coupled through a 90° phase splitter 80 so that real (R) and imaginary (I) portions of the signal are obtained. The double balance mixers 76 and 78 preferably operate at the modulation frequency. The phase ($\theta^\lambda$) is the angle whose tangent is the imaginary over the real part.

$$\theta^\lambda = \tan^{-1} \frac{I^\lambda}{R^\lambda} \quad (18)$$

The amplitude is the square root of the sum of the squares of these values, providing the phase shift has been taken out as the residual phase shift θ set to zero.

$$A^\lambda = \sqrt{(R^\lambda)^2 + (I^\lambda)^2} \quad (19)$$

This embodiment uses summing and dividing circuits to calculate the modulation index, which is the quotient of the amplitude over the amplitude plus the DC component obtained from a narrow band detector 82.

$$M^\lambda = \frac{A^\lambda}{A^\lambda + DC^\lambda} \quad (20)$$

The phase processor receives the phase shifts for the phase and amplitude values for two or three wavelengths and calculates the ratio of the phase shifts. For each wavelength, the phase shift and the DC amplitude are used to determine a selected tissue property, e.g., hemoglobin oxygenation.

Figure 10A:
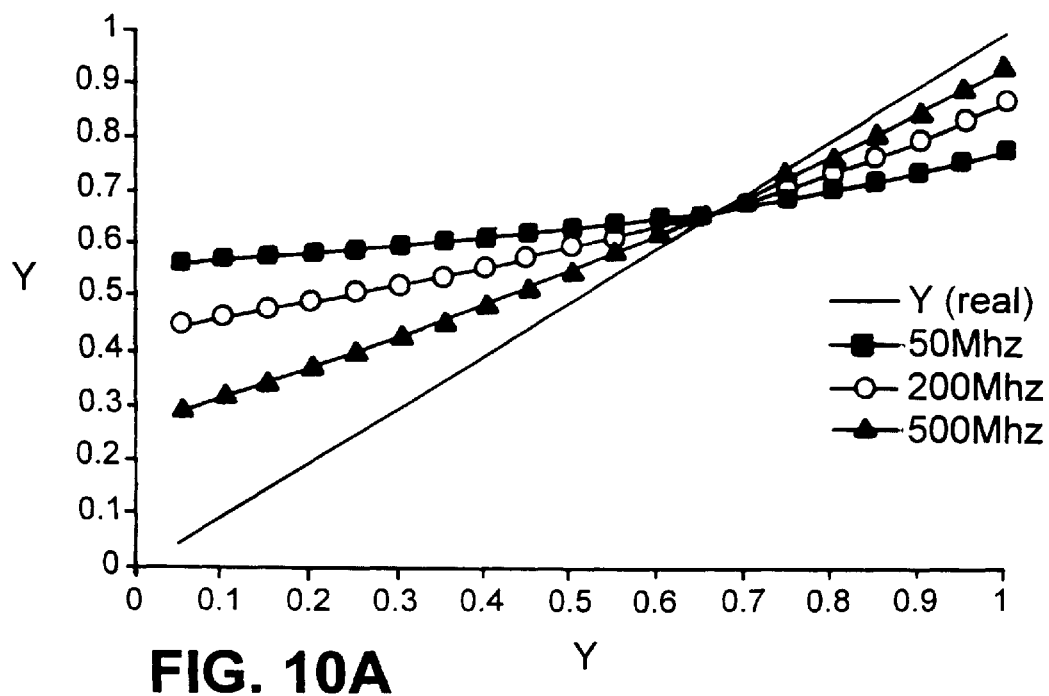
FIGS. 10A and 10B display simulation results for oxygen saturation values and their noise dependence, respectively, calculated by using a high frequency approximation.
Figure 10B:
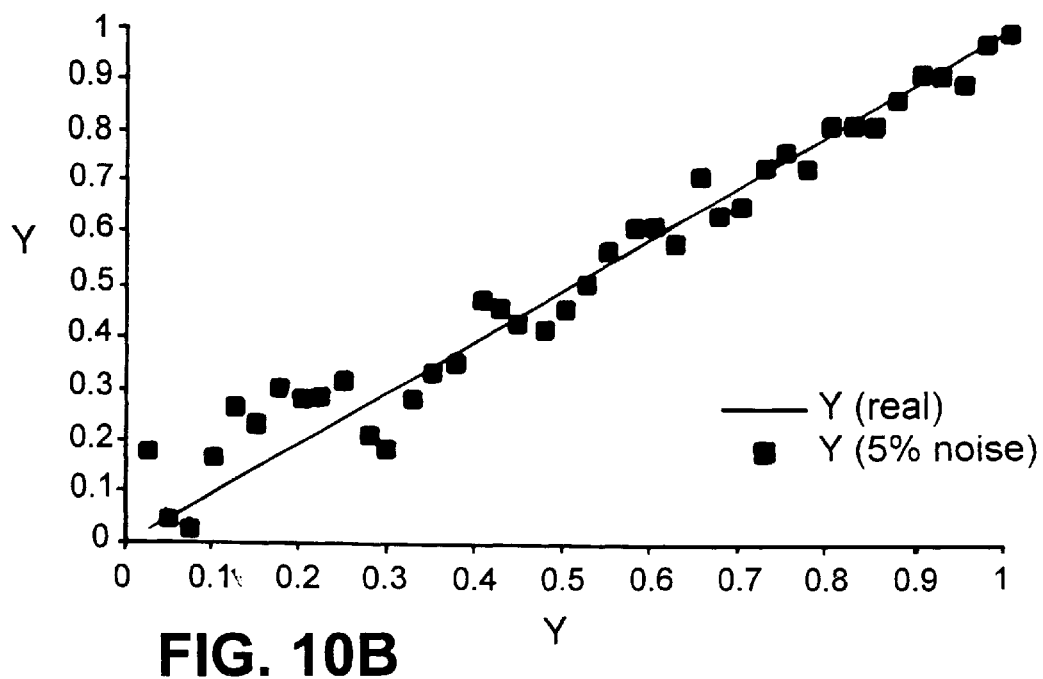

To study the influence of variation in the scattering coefficient on the quantitation of the absorption measurements, several simulations were performed. The simulations assumed the phase shift measurements at two wavelengths and several frequencies (10 MHz, 50 MHz, 200 MHz and 500 MHz). Hemoglobin saturation levels (Y) were varied in the range of 5%≤Y≤100%, and the absorption coefficients were varied in the range of $0.5 \leq \mu_a \leq 1.5$ cm$^{-1}$, while the scattering coefficient $\mu_s'=5$ cm$^{-1}$ was kept constant; these values correspond to typical values for human tissue. FIGS. 10A and 10B show simulation results obtained by using the high frequency approximation ($2\pi f >> \mu_a c$) for modulation frequencies f=50, 200 and 500 MHz, assuming $\theta_0^{\lambda 1} = \theta_0^{\lambda 2} = \theta_0$, and $\mu_a c \approx 2 \cdot 10^9 \cdot \theta_0$. As shown in FIG. 10A, the calculated saturation error decreases with frequency, but still introduces a significant error even for the 500 MHz at low saturation values. FIG. 10B shows the influence of added 5% noise for f=500 MHz. Low saturation values exhibit greater sensitivity to the introduced noise than high saturation values.

The high sensitivity at low saturation values is expected for the high frequency approximation (Eq. 11). While the absorption coefficient for an isobestic wavelength does not change with saturation, lower saturation values yield lower values of the absorption coefficient for a contrabestic oxyhemoglobin wavelength; this yields lower values of $\theta^{\lambda 2} - \theta_0$ in the denominator of Eq. 11. Thus, the $\mu_a$ ratio, at the two wavelengths, is more sensitive to noise at low saturation values.

Figure 11A:
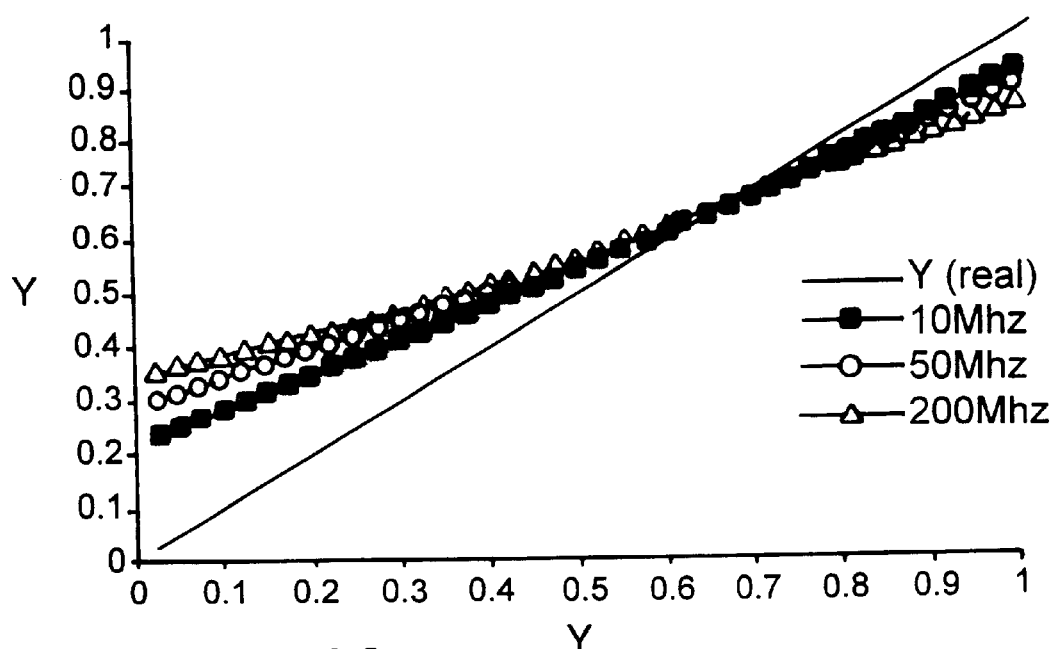
FIGS. 11A and 11B display simulation results for oxygen saturation values and their noise dependence, respectively, calculated by using a low frequency approximation.
Figure 11B:
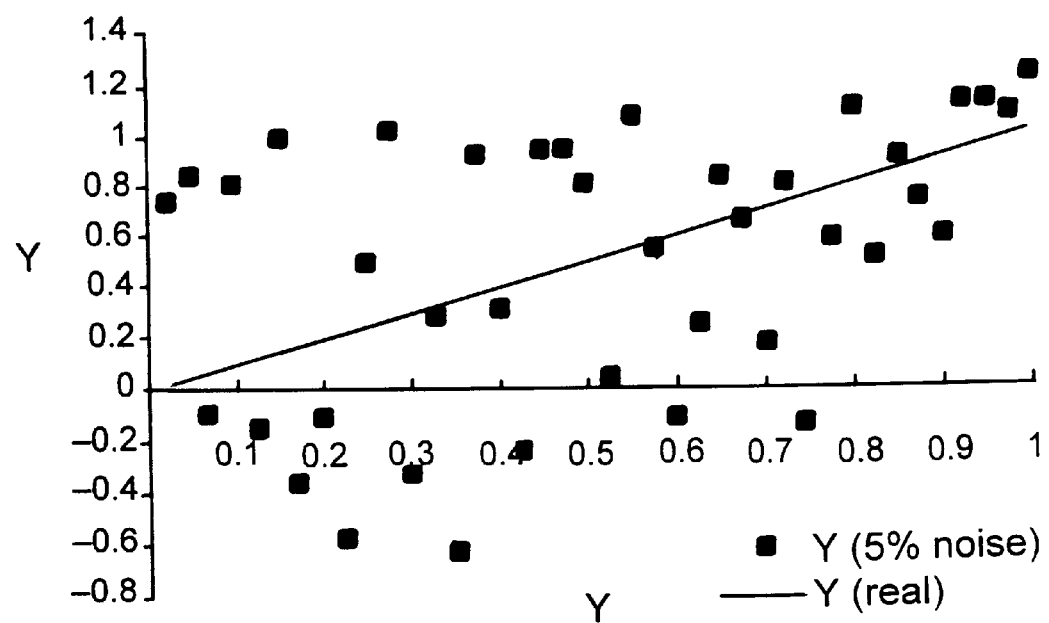

FIGS. 11A and 11B show simulation results obtained using the low frequency approximation ($2\pi f << \mu_a c$) for modulation frequencies f=10, 50 and 200 MHz, assuming $\theta_0^{\lambda 1} = \theta_0^{\lambda 2} = \theta_0$, and $\mu_a c \approx 2 \cdot 10^9 \cdot \theta_0$. As shown in FIG. 11A, the low frequency approximation introduces lower error for the "intermediate" frequency of 200 MHz than the high frequency approximation shown in FIG. 10A. However, the low frequency approximation is much more sensitive to noise as shown in FIG. 11B. The relatively high sensitivity is again expected because the ratio of the absorption coefficients at the two wavelengths is obtained from the square of the phase shift ratio, i.e., $\mu_a^{\lambda 2}/\mu_a^{\lambda 1} = (\theta^{\lambda 1}/\theta^{\lambda 2})^2$.

Thus, when using the high and low frequency approximation, the calculated data may need to be corrected. The correction can be made by using look-up tables or other methods, such as dual frequency phase modulation measurement (Eq. 14) or phase modulation measurements with dual source-detector separation, to obtain more accurate information about the background phase shift.

Figure 12:
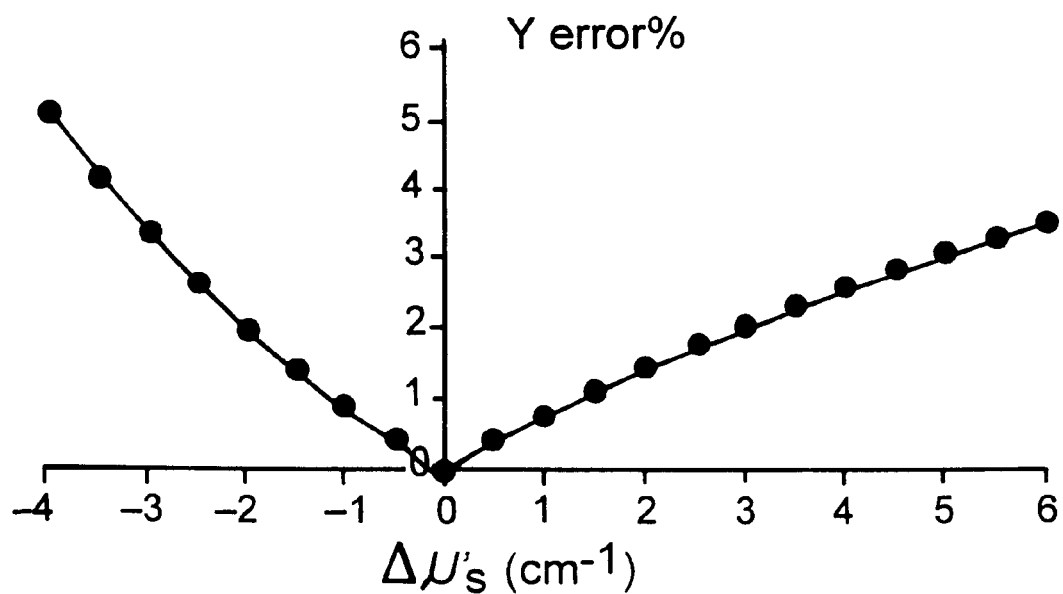
FIG. 12 displays simulation results for oxygen saturation values as a function of a varying scattering coefficient.

FIG. 12 shows simulation results for the oxygen saturation obtained using Eq. 4 to calculate the ratio of absorption coefficients at the two wavelengths. This simulation assumed a correct value of the effective scattering coefficient ($\mu_s'=7$ cm$^{-1}$) and varied the "selected" tissue saturation (and thus the tissue absorption). For each "selected" saturation, the simulation calculated the absorption coefficient solving Eq. 4, while numerically varying $\mu_s'$ from 3 cm$^{-1}$ to 13 cm$^{-1}$ using the Newton-Raphson method. For each $\mu_s'$, the error in the calculated saturation Y was calculated by subtracting the "selected" saturation from the "back-calculated" saturation. As shown in FIG. 12, for example, for a error of 3 cm$^{-1}$ in $\mu_s$, the mean error in Y is about 2.5%, while the standard deviation does not exceed 1.59%. Thus, by employing Eq. 4, the phase modulation system can use an approximate value of the effective scattering coefficient to measure the oxygen saturation. The oxygen saturation is quite insensitive to the selection of the effective scattering coefficient as the introduced error is reduced by taking the ratio of the absorption coefficients.

The phase modulation system is calibrated initially and may be recalibrated after several measurements to obtain a correct phase reading and an average drift. Another type of a phase modulation system is PMD-3000 (available from NIM Incorporated, Philadelphia, Pa.), which is also described in U.S. Pat. No. 5,122,974. This phase modulation system uses two laser diodes at 754 nm and 780 nm, each having an average signal power 5 mW. The two wavelengths are time shared using a mechanical shutter before the light is introduced in the tissue and then detected by a Hamamatsu R928 PMT detector. The system uses two frequencies of 200.000 MHz and 200.025 MHz, and the detected signal is demodulated by heterodyning the second dynode of the PMT detector. The detected amplitude is used in a feed-back loop as an automatic gain control.

The phase detector of the system provides a voltage output that is converted then to the phase as specified by the manufacturer. There are several techniques to determine the voltage-to-phase conversion curve, which ideally should be linear and the precision should be better that 0.1°. The conversion curve can be verified by changing the pathlength of the electrical or optical signal by changing the physical length of an electrical line. Here, one has to watch for a line mismatch that can potentially create measurement problems. Alternatively, the conversion curve can be verified by changing the source detector separation on an optical bench and measuring the corresponding voltage difference at the output of the phase detector. One has to prevent the phase amplitude cross-talk and operate the system at a proper signal-to-noise level.

Alternatively, one can simulate a real experiment by using a tank containing an Intralipid™ solution of known absorption and scattering properties. (See Sevick et al., Analytical Biochemistry Vol. 195, p. 341.) The source-detector geometry resembles the actual tissue measurement geometry. The measured absorption coefficient can thus be compared to the known absorption coefficient. The voltage-to-phase curve is calibrated by taking multiple points at different blood concentrations.

The phase modulation system also has a reference phase ($\theta_{instr}$) that of course affects $\theta_0$. The instrumental reference phase can be determined empirically or can be measured by butt-coupling the source and detector fibers. In this arrangement, the detected optical signal should be attenuated with a neutral density or NTR filter so the detector works in the same signal power range as for the in vivo tissue measurements.

The instrumental reference phase can also be measured using a dual channel phase modulation system that provides both a phase output and an amplitude output. In this measurement, the above model should have similar scattering and no absorption, or known scattering and absorbing properties. The dual channel phase modulation system can resolve both $\mu_s'$ and $\mu_a$, which in turn are used to calculate the instrumental reference phase. Furthermore, the instrumental reference phase can also be determined by measuring the phase shift at different source-detector separations.

The phase modulation system can use the amplitude in a feedback arrangement to control the laser intensity. (This type of feedback is similar to the automatic gain control (AGC) technique described above.) The intensity is adjusted in discrete steps so that no change in the laser intensity occurs during the measurement. This feedback system can measure tissue at a wide range of source-detector separations or background absorptions; there is no need to select an optical attenuator or adjust the gain (high voltage) of the detector. Furthermore, the detector can be operated in the optimum high voltage for all measurements.

In an experimental study, six newborn piglets, age one to five days, were used (average weight—2.0 kg). After anesthesia and surgery, they were randomized either to preexisting mixed acidosis with a pH less than 7.00 and a $PCO_2$ larger than 8.0 kPa, or a normal pH and $pCO_2$. The acidosis was induced by infusing lactic acid in a vein, and $CO_2$ was added to the inspired air. Once the piglets were stabilized, the fraction of oxygen in the inspired air (the $FiO_2$) was reduced from 21% to 6% for 30–40 minutes and then the piglets were resuscitated. Mean arterial blood pressure was kept above 40 mmHg at all times using an intravenous adrenaline infusion.

Figure 13A:
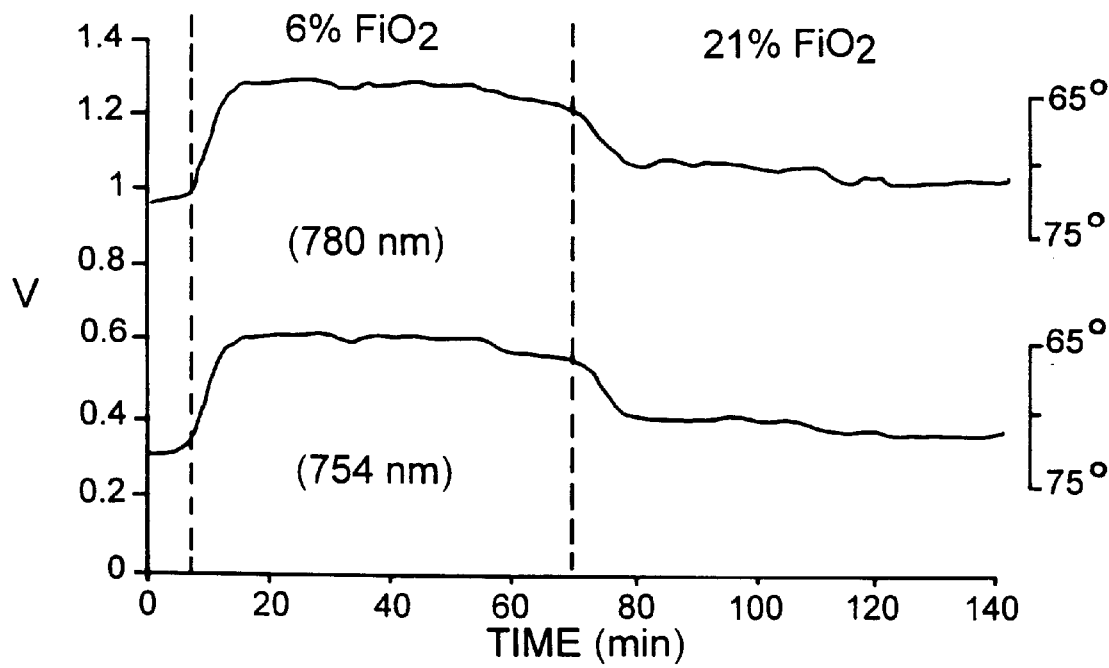
FIGS. 13A and 13B display raw data and calculated saturation data, respectively, measured on a newborn piglet.
Figure 13B:
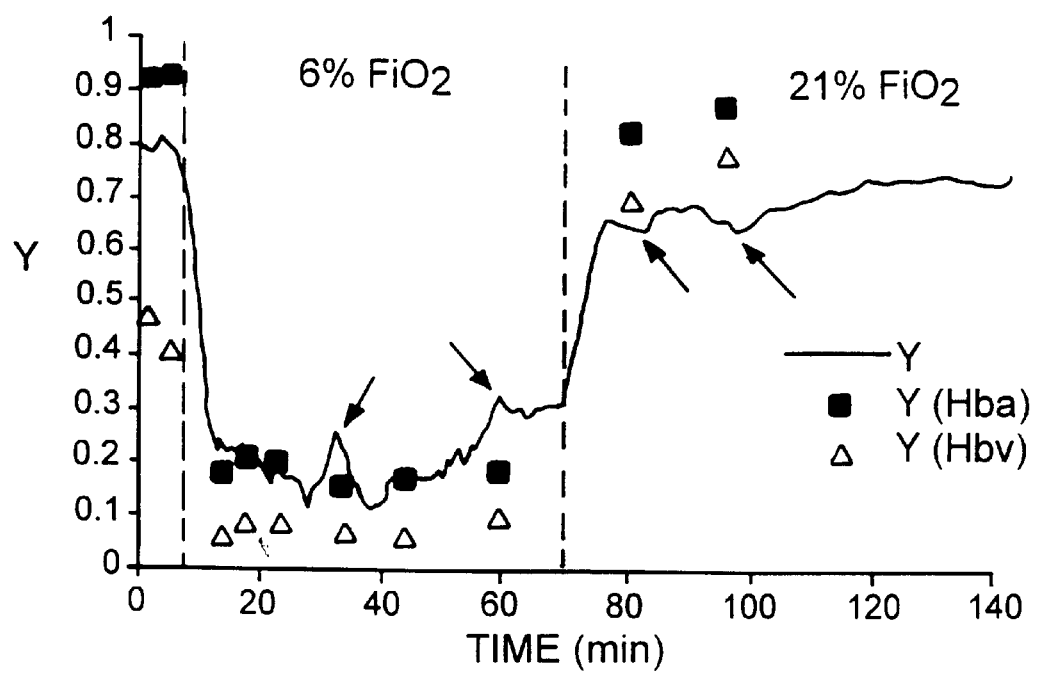

A PMD-3000 system was used to perform the phase modulation measurements. Part of the scull skin was removed and the optical probes were fixed directly to the scull. Typical separations used were 1.7–2 cm. FIGS. 13A and 13B depict the filtered raw data and saturation calculation from a typical measurement. The filtering was done digitally by applying a median filter (kernel size 5) twice followed by a smoothing filter (kernel size 11). The saturation was calculated by numerically solving Eq. 4 for the two wavelengths in order to compute the $\mu_a$ ratio as discussed above. The $\mu_s'$ value for the pigs was selected to be 12 cm$^{-1}$.

During the experimental study, the venous and arterial blood was sampled regularly and blood saturation was immediately calculated. Cerebro-venous saturation values were obtained through an indwelling superior sagittal sinus line and arterial values from a catheter in the femoral artery. The influence of the arterial blood sampling can been seen on FIG. 13B, where the observable sampling points have been marked with arrows, and the local variations are due to the local blood volume changes. The characteristic values of hemoglobin saturation for venous (Hbv) and arterial (Hba) blood are given in FIG. 13B as individual points.

The calculated saturation is somewhat higher than what was expected for the 6% $FiO_2$ interval and lower for the 21% interval. This discrepancy can be correlated by measuring or compensating for water absorption, geometry and scull influence. Furthermore, the extinction coefficients were linearly interpolated for the used wavelengths from charts, and there are random errors introduced in the measurement or derivation of the $\theta_{instr}^{754}$ and $\theta_{instr}^{780}$ which may lead to systematic errors in the calculation.

Additional embodiments are within the following claims:

What is claimed is:

1. An in vivo spectroscopic method for examining biological tissue, comprising:

positioning an input port at a selected location relative to the biological tissue;

positioning a detection port at another location spaced at a selected distance of several centimeters from said input port;

generating a first carrier waveform at a selected frequency on the order of $10^8$ Hz;

introducing into the tissue at said input port electromagnetic radiation of a selected wavelength modulated by said carrier waveform, said wavelength being sensitive to concentration of said absorptive pigment present in the tissue;

detecting at said detection port the radiation that has migrated over migration paths in a portion of the tissue from said input port, said portion of the tissue depending on said locations of said input and detection ports;

comparing the detected radiation with the introduced radiation and measuring therefrom a phase shift ($\theta$) of said detected radiation;

providing a scattering of said portion of the tissue;

using a recursive procedure to calculate a value of the absorption coefficient, at said wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2}c^{-1}}, \psi_\infty = \psi(f=0)$$

$$\Theta = \tan^{-1}\left\{\frac{2\pi f}{\mu_a c}\right\}$$

and examining said tissue portion by using said calculated value of the absorption coefficient.

2. The spectroscopic method of claim 1 wherein said step of providing said scattering property includes generating a second carrier waveform at a second selected frequency on the order of $10^8$ Hz; and measuring said phase shift at said second frequency for each said wavelength.

3. The spectroscopic method of claim 1 wherein said absorptive pigment is oxyhemoglobin or deoxyhemoglobin.

4. The method of claim 1 wherein said examining includes quantifying a concentration of said absorptive pigment in said tissue portion by using said calculated value of the absorption coefficient.

5. The spectroscopic method of claim 1 further comprising;

introducing into the tissue at said input port electromagnetic radiation of a second selected wavelength modulated by said carrier waveform, at least one of said wavelengths being sensitive to concentration of said absorptive pigment present in the tissue, said tissue exhibiting a similar scattering property at said wavelengths;

detecting at said detection port the radiation of said second wavelength that has migrated over migration paths in a portion of the tissue from said input port;

comparing, at said second wavelength, the detected radiation with the introduced radiation and measuring therefrom a phase shift (θ) of said detected radiation at said second wavelength;

using the recursive procedure to calculate a value of the absorption coefficient, at said second wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \psi_\infty = \psi(f=0)$$

$$\Theta = \tan^{-1}\left\{\frac{2\pi f}{\mu_a c}\right\}$$

and said examining includes quantifying the concentration of said absorptive pigment in said tissue portion by using said calculated values of the absorption coefficients at said two wavelengths.

6. The spectroscopic method of claim 5 wherein said quantifying step includes calculating a ratio of absorption coefficients at said two wavelengths; and calculating a value of oxygen saturation based on said ratio.

7. The spectroscopic method of claim 1 wherein said step of providing said scattering property includes looking up a value of said scattering property from a lookup table that includes said values for different tissue types.

8. The spectroscopic method of claim 7 wherein said value of said scattering property is the effective scattering coefficient $(1-g)\mu_s$.

9. The method of claim 1 further including detecting the radiation that has migrated over migration paths in another said portion of the tissue and performing said comparing, said providing and said using the recursive procedure to calculate a value of the absorption coefficient at said wavelength.

10. The method of claim 9 repeated for several said portions of the tissue.

11. A spectroscopic system for examining biological tissue, comprising:

an oscillator constructed to generate a first carrier waveform of a first frequency on the order of $10^8$ Hz;

a light source, operatively coupled to said oscillator, constructed to generate electromagnetic radiation of a selected wavelength modulated by said carrier waveform, said wavelength being sensitive to concentration of said absorptive pigment present in the tissue;

an input port constructed to introduce said radiation into the tissue;

a detection port, located several centimeters apart from said input port, constructed to acquire photons of the radiation that has migrated from said input port over migration paths in a portion of the tissue, said portion of the tissue depending on locations of said input and detection ports;

a detector, optically connected to said detection port, constructed to detect the radiation;

a phase detector constructed to compare the detected radiation with the introduced radiation and determine therefrom the phase shift of said detected radiation; and a processor constructed to receive said phase shift and a scattering property of said portion of the tissue, processor being arranged to use a recursive procedure to calculate a value of the absorption coefficient, at said wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \psi_\infty = \psi(f=0)$$

$$\Theta = \tan^{-1}\left\{\frac{2\pi f}{\mu_a c}\right\}.$$

12. The system of claim 11 including a second oscillator constructed to generate a second carrier waveform of a second selected frequency on the order of $10^8$ Hz;

said source operatively coupled to said second oscillator, constructed to generate electromagnetic radiation of said wavelength modulated by said second carrier waveform;

said detector further constructed to detect the radiation modulated by said second carrier waveform; and said phase detector further constructed to compare, at said wavelength, the detected radiation of said second carrier waveform with the introduced radiation and determine therefrom the phase shift of said detected radiation.

13. The system of claim 11 wherein said absorptive pigment is oxyhemoglobin or deoxyhemoglobin.

14. The system of claim 11 wherein said processor is further arranged to quantify a concentration of said absorptive pigment in said tissue portion by using said calculated value of the absorption coefficient.

15. The system of claim 11 wherein said processor is arranged to use said recursive procedure that involves the Newton-Raphson method.

16. The system of claim 13 wherein said light source is constructed to generate electromagnetic radiation of a second wavelength modulated by said carrier waveform, at least one of said wavelengths being sensitive to said concentration of said absorptive pigment present in the tissue, said tissue exhibiting a similar scattering property at said wavelengths; said detector being constructed to detect the radiation at said second wavelength; said phase detector being constructed to compare the detected radiation with the introduced radiation and determine therefrom the phase shift at said second wavelength; and said processor being constructed to receive said phase shift at said second wavelength and use the recursive procedure to calculate a value of the absorption coefficient, at said second wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \psi_\infty = \psi(f = 0)$$

$$\Theta = \tan^{-1}\left\{\frac{2\pi f}{\mu_a c}\right\}.$$

17. The system of claim 16 wherein said processor is constructed to calculate a ratio of absorption coefficients at said two wavelengths determined by the recursive procedure, and calculate a value of oxygen saturation based on said ratio.

18. The system of claim 11 further including a look up table comprising values of said scattering property for different tissue types.

19. The system of claim 18 wherein said value of said scattering property is the effective scattering coefficient, $(1-g)\mu_s$.

20. An in vivo spectroscopic method for examining biological tissue, comprising:

positioning an input port at a selected location relative to the biological tissue;

positioning a detection port at another location spaced at a selected distance of several centimeters from said input port;

generating a first carrier waveform at a selected frequency on the order of $10^8$ Hz;

introducing into the tissue at said input port electromagnetic radiation of a selected wavelength modulated by said carrier waveform, said wavelength being sensitive to concentration of said absorptive pigment present in the tissue;

detecting at said detection port the radiation that has migrated over migration paths in a portion of the tissue from said input port, said portion of the tissue depending on said locations of said input and detection ports;

creating a first and a second reference phase signals of predefined substantially different phases;

comparing the detected radiation with said first and said second reference signals and determining therefrom a real output signal and an imaginary output signal, respectively;

providing said scattering property of said portion of the tissue;

calculating a value of the phase shift ($\theta$) of said detected radiation as the inverse tangent of the ratio of said imaginary output signal and said real output signal;

using a recursive procedure to calculate a value of the absorption coefficient, at said wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \psi_\infty = \psi(f = 0)$$

$$\Theta = \tan^{-1}\left\{\frac{2\pi f}{\mu_a c}\right\}$$

and examining said tissue portion by using said calculated value of the absorption coefficient.

21. The method of claim 20 wherein said examining includes quantifying a concentration of said absorptive pigment in said tissue portion by using said calculated value of the absorption coefficient.

22. The method of claim 20 further including detecting the radiation that has migrated over migration paths in another said portion of the tissue and performing said comparing, said providing, said calculating and said using the recursive procedure to calculate a value of the absorption coefficient at said wavelength.

23. The method of claim 22 repeated for several said portions of the tissue.

24. The spectroscopic method of claim 20 further comprising introducing into the tissue at said input port electromagnetic radiation of a second selected wavelength modulated by said carrier waveform, at least one of said wavelengths being sensitive to concentration of said absorptive pigment present in the tissue, said tissue exhibiting a similar scattering property at said wavelengths;

detecting at said detection port the radiation of said second wavelength that has migrated over migration paths in a portion of the tissue from said input port;

comparing the detected radiation of said second wavelength with said first and said second reference signals and determining therefrom a real output signal and an imaginary output signal, respectively, at said second wavelength;

calculating a value of the phase shift ($\theta$) of said detected radiation at said second wavelength as the inverse tangent of the ratio of said imaginary output signal and said real output signal using the recursive procedure to calculate a value of the absorption coefficient, at said second wavelength, using the following equation:

$$\theta(\rho, f) = -\psi\sin\frac{\Theta}{2} - \tan^{-1}\frac{-\psi\sin\frac{\Theta}{2}}{1 + \psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \psi_\infty = \psi(f = 0)$$

$$\Theta = \tan^{-1}\left\{\frac{2\pi f}{\mu_a c}\right\}$$

and said examining includes quantifying concentration of said absorptive pigment in said tissue portion by using said calculated values of the absorption coefficients at said two wavelengths.

25. The spectroscopic method of claim 24 wherein said quantifying step includes calculating a ratio of absorption coefficients at said two wavelengths; and calculating a value of oxygen saturation based on said ratio.

26. The spectroscopic method of claim 24 wherein said quantifying step includes calculating, at each wavelength, a detected amplitude (A) as a square root of a sum of squares of said real output signal and said imaginary output signal.

27. The spectroscopic method of claim 24 wherein said step of providing said scattering property includes generating a second carrier waveform at a second selected frequency on the order of $10^8$ Hz; and calculating ($\theta_\lambda$) said phase shift at said second frequency for each said wavelength.

28. A spectroscopic system for examining biological tissue, comprising:

an oscillator constructed to generate a first carrier waveform at a selected frequency on the order of $10^8$ Hz;

a light source, operatively coupled to said first oscillator, constructed to generate electromagnetic radiation of a selected wavelength modulated by said carrier waveform, said wavelength being sensitive to concentration of said absorptive pigment present in the tissue;

an input port constructed to introduce photons of electromagnetic radiation into the examined biological tissue;

a detection port, spaced several centimeters apart from said input port, constructed to acquire photons that have migrated over migration paths in an examined portion of the tissue from said input port, said portion of the tissue depending on locations of said input and detection ports;

a detector constructed to detect, at said detection port, the radiation that has migrated over migration paths in the examined portion of the tissue;

a phase splitter constructed to receive said carrier waveform and produce first and second reference phase signals of predefined substantially different phases;

first and second double balanced mixers connected to receive from said phase splitter said first and second reference phase signals, respectively, and connected to receive from said detector said detector signal, and constructed to produce therefrom a real output signal and an imaginary output signal, respectively; and a processor constructed to receive a scattering property of said portion of the tissue and arranged to calculate a phase shift (θ) of said detected radiation as the inverse tangent of the ratio of said imaginary output signal and said real output signal, said processor being further arranged to use a recursive procedure to calculate a value of the absorption coefficient, at said wavelength, using the following equation:

$$\theta(\rho, f) = -\psi\sin\frac{\Theta}{2} - \tan^{-1}\frac{-\psi\sin\frac{\Theta}{2}}{1+\psi\cos\frac{\Theta}{2}}$$

wherein $$\psi = \sqrt{3(1-g)\mu_s p^2\{(\mu_a c)^2 + (2\pi f)^2\}^{1/2} c^{-1}}, \quad \psi_\infty = \psi(f=0)$$

$$\Theta = \tan^{-1}\left\{\frac{2\pi f}{\mu_a c}\right\}.$$

29. The system of claim 28 including a second oscillator constructed to generate a second carrier waveform of a second selected frequency on the order of $10^8$ Hz;

said source operatively coupled to said second oscillator, constructed to generate electromagnetic radiation of said wavelength modulated by said second carrier waveform;

said detector further constructed to detect the radiation modulated by said second carrier waveform; and said first and second double balanced mixers connected to receive from said phase splitter said first and second reference phase signals, respectively, and connected to receive from said detector said detector signal, and constructed to produce therefrom a real output signal and an imaginary output signal, respectively, at said second frequency.

30. The system of claim 28 wherein said processor is further arranged to quantify a concentration of said absorptive pigment in said tissue portion by using said calculated value of the absorption coefficient.

31. The system of claim 28 wherein said absorptive pigment is oxyhemoglobin or deoxyhemoglobin.

32. The system of claim 28 further including a look up table comprising values of said scattering property for different tissue types.

33. The system of claim 32 wherein said value of said scattering property is the effective scattering coefficient, $(1-g)\mu_s$.

34. The system of claim 28 wherein said light source is constructed to generate electromagnetic radiation of a second wavelengths modulated by said carrier waveform, at least one of said wavelengths being sensitive to said concentration of said absorptive pigment present in the tissue, said tissue exhibiting a similar scattering property at said wavelengths; said detector being constructed to detect the radiation at said second wavelength; said first and second double balanced mixers being connected to receive from said phase splitter said first and second reference phase signals, respectively, and connected to receive from said detector said detector signal, and constructed to produce therefrom, at said second wavelength, a real output signal and an imaginary output signal, respectively; and said processor being arranged to calculate a phase shift (θ) of said detected radiation at said second wavelength, as the inverse tangent of the ratio of said imaginary output signal and said real output signal, said processor being also arranged to use the recursive procedure to calculate a value of the absorption coefficient, at said second wavelength, using the following equation:

$$\theta(\rho, f) = -\psi\sin\frac{\Theta}{2} - \tan^{-1}\frac{-\psi\sin\frac{\Theta}{2}}{1+\psi\cos\frac{\Theta}{2}}$$

wherein $$\psi = \sqrt{3(1-g)\mu_s p^2\{(\mu_a c)^2 + (2\pi f)^2\}^{1/2}c^{-1}}, \psi_\infty = \psi(f=0)$$

$$\Theta = \tan^{-1}\left\{\frac{2\pi f}{\mu_a c}\right\}.$$

35. The system of claim 34 wherein one of said wavelengths is sensitive to oxygenation of hemoglobin and said processor is constructed to calculate a ratio of said absorption coefficients, at said two wavelengths, and calculate therefrom a value of oxygen saturation based on said ratio.

36. The system of claim 34 wherein said processor is arranged to use said recursive procedure that involves the Newton-Raphson method.

* * * * *